(12) United States Patent
Stacey et al.

(10) Patent No.: US 11,175,299 B2
(45) Date of Patent: Nov. 16, 2021

(54) AUTOMATED TRANSPORT UNIT AND SYSTEM

(71) Applicant: THE AUTOMATION PARTNERSHIP (CAMBRIDGE) LIMITED, Hertfordshire (GB)

(72) Inventors: Adrian Stacey, Hertfordshire (GB); Neil Bargh, Hertfordshire (GB); Stuart Tindal, Göttingen (DE)

(73) Assignee: THE AUTOMATION PARTNERSHIP (CAMBRIDGE LIMITED), Hertfordshire (GB)

( * ) Notice: Subject to any disclaimer, the term of this patent is extended or adjusted under 35 U.S.C. 154(b) by 306 days.

(21) Appl. No.: 16/323,754

(22) PCT Filed: Aug. 16, 2017

(86) PCT No.: PCT/EP2017/070783
§ 371 (c)(1),
(2) Date: Feb. 6, 2019

(87) PCT Pub. No.: WO2018/033579
PCT Pub. Date: Feb. 22, 2018

(65) Prior Publication Data
US 2019/0170781 A1   Jun. 6, 2019

(30) Foreign Application Priority Data
Aug. 16, 2016 (EP) .................................. 16184369

(51) Int. Cl.
*G01N 35/04* (2006.01)
*G01N 35/10* (2006.01)
(Continued)

(52) U.S. Cl.
CPC ............... *G01N 35/04* (2013.01); *C12M 1/26* (2013.01); *C12M 1/34* (2013.01);
(Continued)

(58) Field of Classification Search
CPC .... G01N 35/04; G01N 35/10; G01N 27/4167; G01N 2035/0406; G01N 2035/0489; C12M 1/34; C12M 1/26; G05D 1/0212
See application file for complete search history.

(56) References Cited

U.S. PATENT DOCUMENTS 4,047,547 A * 9/1977 Rechtsteiner ......... B65B 39/002
73/863.86
2004/0099334 A1   5/2004 Acker
(Continued)

FOREIGN PATENT DOCUMENTS

WO   WO-03039961 A2   5/2003

OTHER PUBLICATIONS

International Search Report, PCT/EP2017/070783, 3 pages.
Written Opinion of the ISA, PCI/EP2017/070783, 8 pages.

*Primary Examiner* — Jill A Warden
*Assistant Examiner* — John McGuirk
(74) *Attorney, Agent, or Firm* — Adsero IP (57) ABSTRACT

Described is an automated transport unit for use in a laboratory environment the automated transport unit comprising a drive mechanism for moving the automated transport unit, a control system for controlling operation of the automated transport unit, a power supply for powering the automated transport unit, and a storage compartment configured to hold a material obtained from a fluid storage vessel and/or to be delivered to a fluid storage vessel. Also described is a system comprising an automated transport unit and a fluid storage vessel.

22 Claims, 2 Drawing Sheets

(51) Int. Cl.
*G01N 27/416* (2006.01)
*G05D 1/02* (2020.01)
*C12M 1/34* (2006.01)
*C12M 1/26* (2006.01)

(52) U.S. Cl.
CPC ......... *G01N 27/4167* (2013.01); *G01N 35/10* (2013.01); *G05D 1/0212* (2013.01); *G01N 2035/0406* (2013.01); *G01N 2035/0489* (2013.01)

(56) References Cited

U.S. PATENT DOCUMENTS

| | | | |
|---|---|---|---|
| 2006/0120926 A1* | 6/2006 | Takada | B01L 3/50853 422/400 |
| 2006/0210422 A1* | 9/2006 | Roberts | A61L 2/202 422/28 |
| 2007/0128087 A1* | 6/2007 | Cannizzaro | C12M 37/00 422/119 |
| 2009/0004063 A1* | 1/2009 | Higashihara | G01N 35/0099 422/400 |
| 2009/0311772 A1* | 12/2009 | Quinn | C12M 21/12 435/286.5 |
| 2010/0219968 A1 | 9/2010 | Teutenberg | |
| 2014/0150924 A1* | 6/2014 | Nodin | B01L 1/02 141/1 |
| 2014/0373747 A1 | 12/2014 | Yagci et al. | |
| 2015/0276777 A1* | 10/2015 | Riether | G01N 35/10 700/230 |
| 2017/0089936 A1* | 3/2017 | Lee | C12N 15/101 |

* cited by examiner

AUTOMATED TRANSPORT UNIT AND SYSTEM

RELATED APPLICATIONS

This application is a 35 U.S.C. § 371 national phase application of PCT/EP2017/070783 (WO 2018/033579) filed on Aug. 16, 2017, entitled "Automated Transport Unit and System", which is a PCT application of EP-16184369.3 filed on Aug. 16, 2016, which is incorporated herein by reference in its entirety.

FIELD OF THE INVENTION

The present invention relates to an automated transport unit and a system comprising an automated transport unit and a fluid storage vessel such as a reaction vessel.

BACKGROUND TO THE INVENTION

Manual sampling and analysis of samples taken from reaction vessels, such as bioreactors, and the addition of material to such vessels by human operators is inherently problematic and inconsistent. Humans make mistakes and, regardless of training and clear protocols, individuals will make errors and the differences between operators will mean slight differences will always occur. These issues can result in significant errors arising in, for example, sample volume, accuracy and timing, all of which can affect the outcome and understanding of the sampled processes.

Additionally, the sterility of the environment within which the manual sampling by a human operator is carried out is at risk by the very presence of the human operator. Contamination can lead to the loss of material and work if the environment is contaminated. For example, in biopharma production or development, cells can become contaminated by bacteria and, because cells are grown in a very rich media, this is also an ideal environment for bacteria. Once it is in the environment, it is almost impossible to remove bacteria. Thus, all work and material must be disposed of.

Further, a single human operator is not available twenty four hours a day, seven days a week and there are often legal restrictions on the permitted consecutive hours in laboratory environments. Many processes, such as mammalian and microbial processes, run continuously for many days. It is not uncommon for such processes to run for three or more days and for these processes to require continuous sampling and/or addition of material. Where there is a single lab technician working with a particular reaction vessel, gaps in sampling often arise.

To prevent this, increased skilled labour is required to meet the sampling and/or additional requirements of such processes. This increases the associated cost.

Bench top sampling and analysis modules are known which are capable of automatically carrying out specific stages of the sampling and analysis process.

However, no known analysis or sampling module is able come close to match a human operator in terms of versatility and most require a significant degree of preparation in the form of human involvement.

Thus, the above outlined issues with human involvement are not obviated by known bench top sampling and analysis modules.

There is a need for an improved automated sampling and/or addition device and corresponding system which is able to overcome the above outlined disadvantages associated with known methods of sampling and addition of reaction vessels.

SUMMARY OF THE INVENTION

According to a first aspect of the invention, there is provided an automated transport unit for use in a laboratory environment, the automated transport unit comprising: a drive mechanism for moving the automated transport unit; a control system for controlling operation of the automated transport unit; a power supply for powering the automated transport unit; and a storage compartment configured to hold a material obtained from a fluid storage vessel and/or to be delivered to a fluid storage vessel.

Advantageously, such an automated transport unit may be used in place of the skilled labour required in known reaction vessel sampling and/or addition processes to fully automate the whole of a sampling and/or addition process. The accuracy of such processes is greatly increased by use of such an automated transport unit as human error is removed from the equation.

The automated transport unit is also able to carry out such processes twenty four hours a day, seven days a week at no additional cost, as would be the case if human operators were required.

Additionally, it is far easier to maintain a sterile laboratory environment as contamination as a result of human involvement is no longer an issue.

Preferably, the automated transport unit further comprises a material transfer device configured to extract material from a fluid storage vessel and/or add material to a fluid storage vessel.

Preferably, the material transfer device further comprises a pump or syringe configured to remove material from a fluid storage vessel and/or add material into a fluid storage vessel.

Preferably, the storage compartment further comprises a temperature controlled area configured to store material during transit. This helps maintain the material in a state suitable for transport as degradation is minimised if the sample is kept at a lower temperature.

Preferably, the storage compartment further comprises a biological safety compartment suitable for the storing and containment of biological material in an aseptic manner.

Preferably, the automated transport unit further comprises a sterilizing device configured to sterilize a connection port of a fluid storage vessel prior to extracting material from a fluid storage vessel and/or adding material to a fluid storage vessel.

Preferably, the automated transport unit further comprises an analyzing device for analyzing material obtained from a fluid storage vessel.

Preferably, the analyzing device further comprises a pH measuring device and or a dissolved oxygen measuring device.

Preferably, the automated transport unit further comprises a tool for removing a cover cap of a connection port of a fluid storage vessel.

Preferably, the automated transport unit further comprises a detector for detecting if movement of the automated transport unit is blocked.

Preferably, the automated transport unit further comprises a treatment apparatus configured to perform a treatment on material obtained from a fluid storage vessel and/or to be delivered to a fluid storage vessel and, optionally, wherein the treatment apparatus is configured to perform a dilution or acidification of material obtained from a fluid storage vessel and/or to be delivered to a fluid storage vessel.

Preferably, the storage compartment is a centrifuge tube or a disposable syringe.

Preferably, the storage compartment is removable from the automated transport unit.

Preferably, the storage compartment is configured to be loaded onto and/or unloaded from the automated transport unit at one or more stations.

Preferably, the fluid storage vessel is a reaction vessel or a bioreactor.

According to a second aspect of the invention, there is provided a system comprising: a fluid storage vessel; and the automated transport unit according to the first aspect of the invention, wherein the automated transport unit is configured to extract material from the fluid storage vessel and/or deliver material to a fluid storage vessel.

Preferably, the system further comprises an analyzing station, wherein the automated transport unit is configured to transport material to the analyzing station for analysis of the material.

Preferably, the fluid storage vessel and analyzing station are coded so that the automated transport unit can verify its location.

Preferably, the system further comprises a guidance system for guiding the movement of the automated transport unit.

Preferably, the guidance system is one or more of a rail track, a wired controller and a wireless controller.

Preferably, the system further comprises a recharging station for recharging the power supply of the automated transport unit.

Preferably, the fluid storage vessel is a reaction vessel or a bioreactor.

BRIEF DESCRIPTION OF THE DRAWINGS

Embodiments of the present invention will now be described, by way of example only, with reference to the accompanying drawings, in which.

DETAILED DESCRIPTION

The features of the automated transport unit will first be described, with reference to FIG. 1, followed by the features of the wider system within which the automated transport unit operates.

Figure 1:
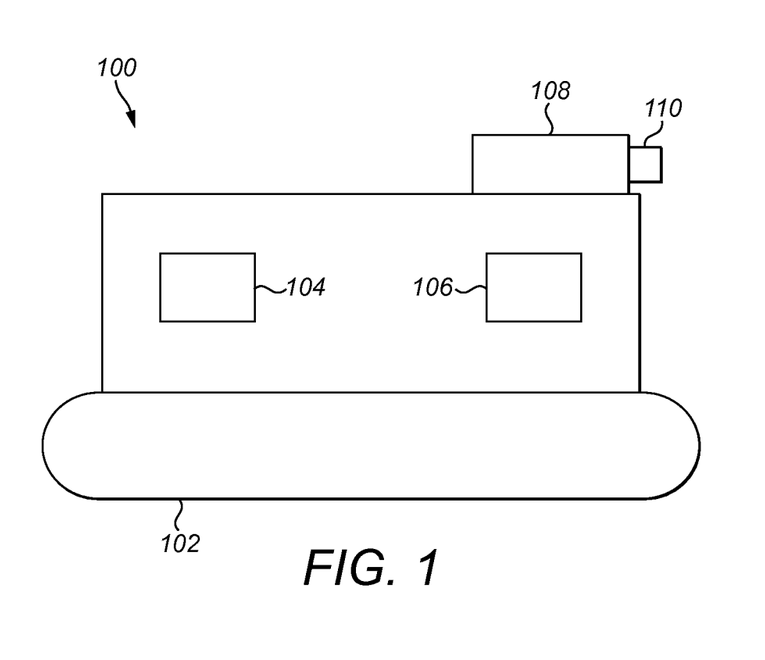
FIG. 1 depicts an automated transport unit according to an embodiment.

FIG. 1 depicts an automated transport unit 100 according to an embodiment of the present invention. The automated transport unit 100 is suitable for use in a laboratory environment. The automated transport unit 100 may be in the form of a robot or rover. The specific features of the automated transport unit 100 will now be described.

The automated transport unit 100 comprises a drive mechanism 102 for moving the automated transport unit around a laboratory environment. The drive mechanism shown 102 in FIG. 1 comprises a track, however, any suitable drive mechanism such as wheels, rollers may be used, as would be understood by the skilled person. The drive mechanism 102 may further comprise an electrical or mechanical drive unit, such as an electric motor. The drive mechanism 102 may comprise a means for magnetically moving the automated transport unit around a laboratory environment.

The automated transport unit 100 further comprises a control system 104 for controlling operation of the automated transport unit. The control system 104 may be in the form of a controller being part of the automated transport unit and/or may be in the form of a wireless or wired transceiver configured to transmit and/or receive control signals from a remote control system of hub.

The control system 104 may be in the form of an on-board processor suitable for carrying out the various operations of the automated transport unit 100 described herein. The on-board processor may be suitable for receiving instructions from a remote control system or hub and carrying out operations based on those instructions. The on-board processor may be suitable for receiving inputs from other elements of the automated transport unit 100 and carrying out and carrying out operations based on those inputs.

The automated transport unit further comprises a power supply 106. The power supply 106 may be in the form of a rechargeable or single use battery. The power supply 106 may also be in the form of a wired power supply, i.e. a power lead connected to a remote power source. The power supply 106 may comprise an electrical cable or an alternative clean power source.

The automated transport unit 100 further comprises a storage compartment 108 configured to store, hold or otherwise retain material or samples obtained from a reaction vessel and/or material for delivery to a reaction vessel. The storage compartment may be adapted in such a way that the material or samples are held temporarily to enable fast retrieval whilst still enabling safe, secure and optionally sterile transport. The compartment may be for long term storage but the primary purpose is to facilitate fast and reliable movement from source to destination. The storage compartment 108 may comprise an Eppendorf tube, syringe single use bag, or any other suitable sample retaining means.

The storage compartment 108 may comprise a centrifuge tube or a disposable syringe.

The storage compartment 108 may be removable from the automated transport unit 100.

The storage compartment 108 may be configured to be loaded onto and/or unloaded from the automated transport unit 100 at one or more stations.

The storage compartment 108 may be in the form of a cassette or cartridge which is removable from the automated transport unit 100.

The reaction vessel with which the automated transport unit 100 is designed to interface so as to add or remove a sample may be a fluid storage vessel, a bioreactor or any other type of reaction vessel as would be understood by the skilled person. The reaction vessel may be a single use or reusable bioreactor or a mixing bag.

Where the term reaction vessel is used to describe a particular vessel herein, it will be understood that a fluid storage vessel, a bioreactor or any other type of reaction vessel could be used in place of the reaction vessel.

Where the terms 'material' or 'samples' obtained from a reaction vessel and/or material for delivery to a reaction vessel, it will be understood that the two terms are interchangeable.

In order to add of remove samples from a reaction vessel, the automated transport unit 100 may further comprise a material transfer device 110 for extracting material or a sample from a reaction vessel and/or adding material or a sample to a reaction vessel.

The material transfer device 110 may further comprise a pump or syringe (not shown in FIG. 1) configured to remove material from a reaction vessel and/or add material into a reaction vessel. The pump or syringe may be a peristaltic pump for pumping liquid to or from a reaction vessel or it may be a syringe pump for pumping liquid to or from a reaction vessel.

In order to retain any such material or sample, for example during transit of the automated transport unit 100, the material transfer device 110 may be in fluid communication with the storage compartment 108 such that material or samples extracted from a reaction vessel can be transmitted to the storage compartment 108 for storage and/or such that material stored in the storage compartment 108 can be transmitted to a reaction vessel via the material transfer device 110. The fluid communication may be in the form of fluid lines, such as tubes.

Alternatively, the material transfer device 110 and the storage compartment 108 may be in the form of a single device in which the material or samples extracted from a reaction vessel are stored. For example, where the material transfer device 110 is a syringe, the syringe itself may also act as the storage compartment 108.

The storage compartment 108 and transfer device 110 may together form a self-contained disposable compartment controllable by the control system 104.

The transfer device 110 may be configured to withdraw material from a reaction vessel for interim storage in the storage compartment 108 or on-board analysis of the material, as will be described in greater detail below.

The transfer device 110 may be configured to clear material from fluid lines of the automated transport unit 100 to allow multiple dockings by the automated transport unit 100 with reaction vessels containing different materials. The automated transport unit 100 may have a waste liquid container (not shown) and, after the transfer device 110 has interfaced with a sampling port of a reaction vessel, a volume of liquid may initially be pumped to the waste liquid container such that any residual material in the lines is cleared. Subsequently, freshly drawn liquid from the vessel may be directed to the storage compartment 108. In this way, cross contamination of material or samples taken from reaction vessels is avoided.

The transfer device 110 may also be arranged to maintain the sterility of the vessel. Examples of this arrangement include a specific sterilizing device, a sterilizing spray and protective coverings. More specific examples will now be described.

The automated transport unit 100 may further comprise a sterilizing device (not shown in FIG. 1) to sterilize a connection port of a reaction vessel prior to extracting material from a reaction vessel and/or adding material to a reaction vessel. This reduces the risk of any contamination of material or samples and the reaction vessel. The sterilizing device minimises the risk of contamination of the vessel.

Where the automated transport unit 100 is to be engaged with a sample port of a bioreactor or other type of reaction vessel, the sterilizing device of the automated transport unit 100 may spray the sample port with a solution or dip the sample port into a compartment, vessel or the like containing a solution thereby sterilizing the sample port. Sterilization of the sample port may be carried out by the automated transport unit 100 using a sterilizing solution, heat, steam, radiation or otherwise prior to connection and/or following disconnection, with the sterilizing device of the automated transport unit 100 appropriated adapted to carry out the sterilization, as would be understood by the skilled person.

The automated transport unit 100 may further comprise a tool (not shown in FIG. 1) for removing a protective cover cap of a connection/sample port of a reaction vessel. The automated transport unit 100 may use the tool to remove a protective cap from the sample port before sampling and to replace it following sampling. Such a cap would help maintain the sterility of the reaction vessel port.

The automated transport unit 100 may also create a sterile filtered clean air environment around the reaction vessel connection port and the transfer device 110 before, during and/or after the sampling procedure to further reduce the chance of contamination.

In further exemplary embodiments, the transfer device 110 may comprise an aseptic sampler or a needless connector for connecting with a reaction vessel.

The transfer device 110 may also comprise one or more of a tube, tube holder, filter, sterile filter and/or a pump, such as a syringe pump, for withdrawing material from a reaction vessel by generating suction.

The transfer device 110 may comprise a needle and/or a syringe (not shown).

The syringe may be arranged to be used in conjunction with a needleless connector on a sample port of a reaction vessel.

Optionally, samples taken from a reaction vessel may be stored in the syringe, where the syringe acts as a storage compartment 108.

The transfer device 110 may be configured to withdraw material through a septum or sterile barrier where the automated transport unit 100 comprises a means for powered piercing of the sample port of the reaction vessel. The means for powered piercing may be a powered mechanical arm for engaging and disengaging a sample port over multiple degrees of freedom and angles.

Both the acceptor port and the receiver port need to match in either a genderless fashion or a male-female lock and key.

Dialysis

Baseline solution pumped around a circulation loop in the vessel where a permeable membrane in the vessel allows molecules to cross into the baseline solution. This would be a defined transport buffer where no molecules of interest are present and the rest of the liquid components make up an isotonic and safe biologically free solution.

As mentioned above, a storage compartment 108 is included within the unit 100 to hold material that has been collected before the transfer device 110 preferably moves the material to another location. Of course, the material could be removed manually but prior to removal the storage compartment 108 may be configured to have particular characteristics depending on the context in which the unit 100 is to be utilised.

For example, the storage compartment 108 may further comprise a temperature controlled area (not shown in FIG. 1) configured to store material or a sample during transit. This helps maintain the material in a state suitable for transport. When taking samples and analyzing them after a known time, the degradation of the sample is more predictable if the sample is housed in a temperature controlled environment. Additionally, degradation is minimised if the sample is kept at a lower temperature.

The storage compartment 108 may further comprise a storage safety compartment (not shown in FIG. 1) which may be in the form of a biological safety compartment suitable for storing and containment of biological material in a septic manner. When taking samples of cells, this also prevents samples from being contaminated by bacteria before being analyzed.

Having described the material or sample transfer and storage features of the automated transport unit 100, the features which enable the automated transport unit 100 to analyze material or samples on-board will now be described. Each feature may be included on the unit 100 or may be left out or otherwise operator configured for each application. The features are not mutually exclusive.

The automated transport unit 100 may further comprise an analyzing device (not shown in FIG. 1), which may further comprise a sensor or a sensor array, for analyzing material obtained from a reaction vessel. Part of or all of the material being transported may pass through the analyzing device so as to undergo analysis. In this way, examination of samples may be carried out on-board or even while the vehicle is in transit.

The analyzing device may be configured to automatically prepare material in a defined way (i.e. dilution, inactivation).

Additionally, analytic instruments may be configured or the unit 100 otherwise coupled in order to directly analyze material, store data onto an on-board memory, process the data on-board or send the data to a central processor which may be remote from the automated transport unit 100.

The analyzing device may further comprise a pH measuring device configured to measure the pH of the material in the analyzing device (or of the material contained by the fluid lines of the automated transport unit 100).

The automated transport unit 100 may be arranged to calibrate or adjust an in-line probe to the vessel from the data it acquires from the sample.

The analyzing device may further comprise one or more of a spectrometer, pH sensor, pO sensor, pCO2 sensor and the like.

A further feature of the automated transport unit 100 is that it may be configured to adjust the volume/mass of material extracted from a reaction vessel or to be added to a reaction vessel, for example by adjusting the length of time for which the transfer device 110 operates in response to a command generated by the control system 104.

The automated transport unit 100, through its control system 104, may be configured to take different sample volumes and this may be determined by the control system 104. Given the variability in sample volume requirements of on-board and external analyzers and the variability in volume of reaction vessels, it is advantageous to allow the automated transport unit 100 to be able to take variable sample volumes.

For example, where the reaction vessel is a 1 L vessel, the control system 104 may control the transfer device 110 such that a 10 mL sample is taken, whereas from a 100 L vessel, the control system 104 may control the transfer device 110 such that a 50 mL sample is taken.

The configuration of the storage compartment 108 and/or the pump time/size may be varied, for example in response to instructions from the control system 104, in accordance with the desired sample volume. This may be done in real time as the automated transport unit 100 is being operated.

Means by which the unit 100 may be able to determine its location could also be included, for example, the automated transport unit 100 may further comprise a location determining device, which may further comprise sensor or a sensor array, for determining the location of the automated transport unit 100. The location determining device may be suitable for determining the location of the automated transport unit 100 relative to other components of the wider system in which it operates or to its location in space through triangulation of GPS. Conventional location determination methods are contemplated and will not be described in detail here.

The automated transport unit 100 may further comprise a detector or sensor (not shown in FIG. 1) for detecting if movement of the automated transport unit is blocked and generating an error message or alarm. The message may be transmitted to an operator remotely.

The automated transport unit 100 may further comprise a treatment apparatus (not shown in FIG. 1) configured to perform a treatment of material obtained from or to be added to a reaction vessel, for example by adding an additive to the sample. Optionally, the treatment apparatus is configured to perform a dilution or acidification of material obtained from or to be added to a reaction vessel.

One option to slow the degeneration of the sample is to cool the sample, as discussed above. However, some applications may require treatment of the sample, for example by adding something to the sample, to stop or reduce this degradation such as an enzyme inhibitor or an organic solvent.

In addition to including one or more of the above outlined features, the automated transport unit 100 may further comprise an guide means in the form of an engagement element, a sensor and/or a processor (not shown in FIG. 1) for engaging and/or interacting with a guidance system, which may be in the form of a rail or track, in such a way that the movement of the automated transport unit 100 is constrained by the guidance system and is guided to locations by rails or tracks.

The automated transport unit 100 may alternatively move around a laboratory environment in an unconstrained manner but the control system may include predefined navigational paths or markers.

The guide means may be configured to interact with electric cables fibre optic cables or optical lines which guide the automated transport unit 100 to predetermined locations.

The guide means may comprise feedback software for orientation in a defined environment. The software may include environmental maps or GPS interfaces. The automated transport unit 100 may include sensors for orientation and correction, effectors for performing moves and activity.

Where the power supply 106 comprises a rechargeable battery, the automated transport unit 100 may further comprise a port and/or wireless charging means (not shown in FIG. 1) via which the rechargeable battery can be recharged.

A specific embodiment of the wider system within which the above described automated transport unit 100 can operate will now be described with reference to FIG. 2.

Figure 2:
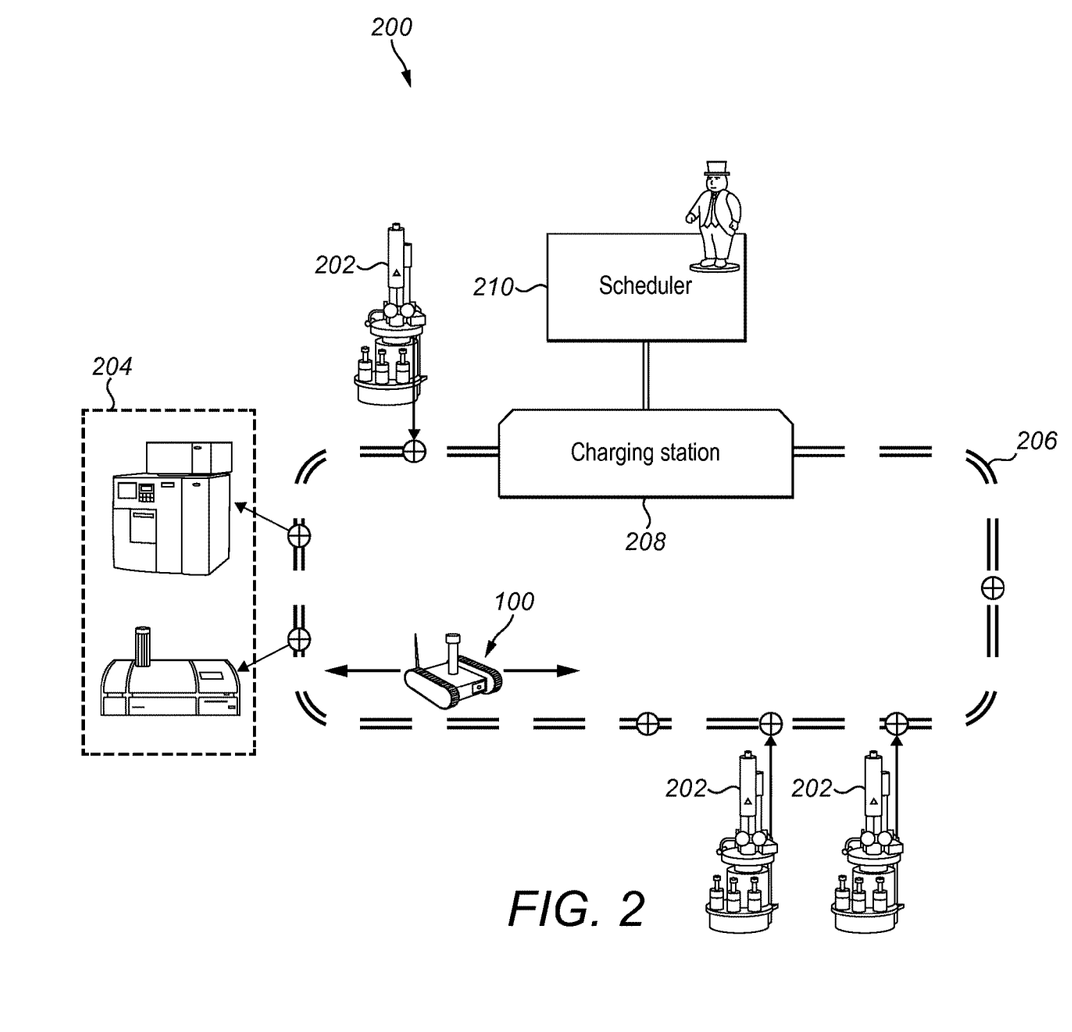
FIG. 2 depicts a system according to an embodiment.

FIG. 2 depicts an example system 200 according to an embodiment of the present invention which represents an example laboratory environment comprising a fluid storage. The system comprises an automated transport unit 100 according to any of the embodiments described herein which functions to transport fluid from one location to another in an automated, yet reliable manner.

The system 200 includes at least one fluid storage vessel such as a reaction vessel 202. The vessel may be a bioreactor. The reaction vessel may be a stirred tank or a rocking motion bag type bioreactor. The reaction vessel may be a single use bioreactor.

The automated transport unit 100 of the system 200 is configured to extract material from the reaction vessel and/or deliver material to the reaction vessel.

The system 200 may further comprise an analyzing station 204 and the automated transport unit 100 may be configured to transport material to the analyzing station 204 for analysis of the sample and/or to transport a sample from the analyzing station 204 once it has been analyzed.

In this example, the reaction vessel 202 and analyzing station 204 may be coded so that the automated transport unit 100 can verify its location when it is at the reaction vessel 202 and/or the analyzing station 204.

To navigate to that location, the system 200 includes a guidance system 206 for guiding the movement of the automated transport unit 100 as described above. In this example, the guidance system comprises a rail or track (as shown in FIG. 2), a wired controller and/or a wireless controller.

Alternatively, the guidance system 206 may comprise electric cables fibre optic cables or optical lines which guide the automated transport unit 100 to predetermined locations.

Alternatively, the he guidance system 206 may comprise a fully automated driving unit comprising feedback software for orientation in a defined environment. The software may include environmental maps or GPS interfaces The illustration of FIG. 2 shows that the system 200 may further comprise a charging station 208. The charging station 208 may be for recharging the power supply 106 of the automated transport unit 100.

The charging station 208 may be in the form of a centralised hub where power, water, additional storage compartments 108 and other consumables can be loaded and unloaded to the automated transport unit 100.

The charging station 208 may comprise an area where material and/or storage compartments 108 can be discarded in an automated process.

The charging station 208 may be configured to recognise and service multiple automated transport units 100 working in the same laboratory environment.

The charging station 208 may be the main information coordination hub where data is routed through to all other points.

Various options may be applied for Open Platform Communications (OPC), Structured Query Language (SQL) and connection to multiple software and hardware architectures.

A software inference which allows communication between other systems such that sample identification information, times, vessel status and sample information is routed around the process control architecture such that changes can be implemented by the hardware, e.g. to turn on a pump or to initiate a sample or to turn off a system.

The system 200 may further comprise a scheduler 210, which is advantageous where the system 200 comprises multiple reaction vessels 202 and analyzing stations 204 and possibly multiple automated transport units 100. The scheduler 210 is arranged to calculate the time the, or each, automated transport unit 100 has to travel, take samples and deliver samples. In essence the logistics planning is handled by the scheduler 210.

The automated transport unit 100 may further comprise an updatable internal clock that ensures synchronized timing. Time changes and new systems should all be on the same time to ensure the correct sample logging details. This helps ensure that Good Laboratory Practice (GLP) and Good Manufacturing Practice (GMP) regulatory requirements are met.

Material can be delivered to another location as e.g. a machine or a lab for further analysis.

Advantageously, in the system described herein, material is transported under the automated transport unit's own power and guided to the correct location.

A Robotic effector may be provided for uploading material-docking interface onto a loading station or analysis module.

All movable, effecting or transporting means (motor; valve; pump, telescopic actors and there like) may be coordinated by the robotic effector and loading interface combination.

Communication and data on the material identity will be uploaded to the loading/analysis module automatically via the Rover central hub.

There may not be a "central hub" as such. Data transfers are likely to be via Wifi/Bluetooth or similar over a distributed network but the data may be stored in a database. The data transfers are likely to occur in real time as actions are occurring. Physically, there could be multiple charging stations, (it may be possible to also charge at a reaction vessel).

The automated transport unit 100 may be configured to perform an automated loading method which may be carried out by the control system 104 of automated transport unit 100, the method having one or more of the following steps:

Determining whether the automated transport unit 100 is at a loading destination by analyzing a signal from the location determining device;

Facilitating a 2-way time stamp by sending a signal indicating when action is being performed at the loading destination to a central processor which may be remote from the automated transport unit 100;

Sending a signal to the material transfer device 110 causing it to move material into the storage compartment 108 from the reaction vessel 202 or the analyzing station 204; and/or The automated transport unit 100 may be configured to perform an automated unloading method which may be carried out by the control system 104 of automated transport unit 100, the method having one or more of the following steps;

Determining whether the automated transport unit 100 is at an unloading destination by analyzing a signal from the location determining device;

Facilitating a 2-way time stamp by sending a signal indicating when action is being performed at the loading destination to a central processor which may be remote from the automated transport unit 100;

Sending a signal to the material transfer device 110 causing it to move material from the storage compartment 108 to the reaction vessel 202 or to the analysis station 204 of the system 200.

Generally, any of the functionality described in this text or illustrated in the figures can be implemented using software, firmware (e.g., fixed logic circuitry), programmable or non-programmable hardware, or a combination of these implementations.

Methods and processes described herein can be embodied as code (e.g., software code) and/or data. Such code and data can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium. In certain embodiments, one or more of the steps of the methods and processes described herein can be performed by a processor (e.g., a processor of a computer system or data storage system). It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals.

The invention claimed is:

1. An automated transport unit for use in a laboratory environment, the automated transport unit comprising:
    a drive mechanism for moving the automated transport unit;
    a control system for controlling operation of the automated transport unit;
    a power supply for powering the automated transport unit; and
    a storage compartment configured to hold a material obtained from a fluid storage vessel and/or to be delivered to a fluid storage vessel;
    wherein:
    the storage compartment further comprises a biological safety compartment suitable for the storing and containment of biological material in an aseptic manner;
    the automated transport unit further comprising a material transfer device configured to extract material from the fluid storage vessel and/or add material to the fluid storage vessel, the material transfer device being arranged to maintain the sterility of the fluid storage vessel;
    the automated transport unit further comprising a sterilizing device configured to sterilize a connection port of the fluid storage vessel prior to extracting material from the fluid storage vessel and/or adding material to the fluid storage vessel; and
    the material transfer device further comprising a pump or syringe configured to remove material from the fluid storage vessel and/or add material into the fluid storage vessel.

2. The automated transport unit of claim 1, wherein the storage compartment further comprises a temperature controlled area configured to store material during transit.

3. The automated transport unit of claim 1, the automated transport unit further comprising an analyzing device for analyzing material obtained from the fluid storage vessel.

4. The automated transport unit of claim 3, wherein the analyzing device further comprises a pH measuring device and/or a dissolved oxygen measuring device.

5. The automated transport unit of claim 1, the automated transport unit further comprising a detector for detecting if movement of the automated transport unit is blocked.

6. The automated transport unit of claim 1, the automated transport unit further comprising a treatment apparatus configured to perform a treatment on material obtained from the fluid storage vessel and/or to be delivered to the fluid storage vessel and, optionally, wherein the treatment apparatus is configured to perform a dilution or acidification of material obtained from the fluid storage vessel and/or to be delivered to the fluid storage vessel.

7. The automated transport unit of claim 1, wherein the storage compartment is a centrifuge tube or a disposable syringe.

8. The automated transport unit of claim 1, wherein the storage compartment is removable from the automated transport unit.

9. The automated transport unit of claim 1, wherein the storage compartment is configured to be loaded onto and/or unloaded from the automated transport unit at one or more stations.

10. A system comprising:
    a fluid storage vessel; and
    an automated transport unit, comprising:
    a drive mechanism for moving the automated transport unit;
    a control system for controlling operation of the automated transport unit;
    a power supply for powering the automated transport unit; and
    a storage compartment configured to hold a material obtained from the fluid storage vessel and/or to be delivered to the fluid storage vessel;
    wherein:
    the storage compartment further comprises a biological safety compartment suitable for the storing and containment of biological material in an aseptic manner;
    the automated transport unit further comprising a material transfer device configured to extract material from the fluid storage vessel and/or add material to the fluid storage vessel, the material transfer device being arranged to maintain the sterility of the fluid storage vessel;
    the automated transport unit further comprising a sterilizing device configured to sterilize a connection port of the fluid storage vessel prior to extracting material from the fluid storage vessel and/or adding material to the fluid storage vessel; and
    the material transfer device further comprises a pump or syringe configured to remove material from the fluid storage vessel and/or add material into the fluid storage vessel.

11. The system of claim 10, the system further comprising an analyzing station, wherein the automated transport unit is configured to transport material to the analyzing station for analysis of the material.

12. The system of claim 11, wherein the fluid storage vessel and analyzing station are coded so that the automated transport unit can verify its location.

13. The system of claim 10, the system further comprising a guidance system for guiding the movement of the automated transport unit.

14. The system of claim 13, wherein the guidance system is one or more of a rail track, a wired controller and a wireless controller.

15. The system of claim 10, the system further comprising a recharging station for recharging the power supply of the automated transport unit.

16. The system of claim 10, wherein the fluid storage vessel is a reaction vessel or a bioreactor.

17. An automated transport unit for use in a laboratory environment, the automated transport unit comprising:
    a drive mechanism for moving the automated transport unit;
    a control system for controlling operation of the automated transport unit;
    a power supply for powering the automated transport unit; and
    a storage compartment configured to hold a material obtained from a fluid storage vessel and/or to be delivered to a fluid storage vessel;

wherein:
the storage compartment further comprises a biological safety compartment suitable for the storing and containment of biological material in an aseptic manner;
the automated transport unit further comprising a material transfer device configured to extract material from the fluid storage vessel and/or add material to the fluid storage vessel, the material transfer device being arranged to maintain the sterility of the fluid storage vessel;
the automated transport unit further comprising a sterilizing device configured to sterilize a connection port of the fluid storage vessel prior to extracting material from the fluid storage vessel and/or adding material to the fluid storage vessel; and
the storage compartment further comprises a temperature controlled area configured to store material during transit.

18. An automated transport unit for use in a laboratory environment, the automated transport unit comprising:
a drive mechanism for moving the automated transport unit;
a control system for controlling operation of the automated transport unit;
a power supply for powering the automated transport unit; and
a storage compartment configured to hold a material obtained from a fluid storage vessel and/or to be delivered to a fluid storage vessel;
wherein:
the storage compartment further comprises a biological safety compartment suitable for the storing and containment of biological material in an aseptic manner;
the automated transport unit further comprising a material transfer device configured to extract material from the fluid storage vessel and/or add material to the fluid storage vessel, the material transfer device being arranged to maintain the sterility of the fluid storage vessel;
the automated transport unit further comprising a sterilizing device configured to sterilize a connection port of the fluid storage vessel prior to extracting material from the fluid storage vessel and/or adding material to the fluid storage vessel; and
the automated transport unit further comprising an analyzing device for analyzing material obtained from the fluid storage vessel.

19. An automated transport unit for use in a laboratory environment, the automated transport unit comprising:
a drive mechanism for moving the automated transport unit;
a control system for controlling operation of the automated transport unit;
a power supply for powering the automated transport unit; and
a storage compartment configured to hold a material obtained from a fluid storage vessel and/or to be delivered to a fluid storage vessel;
wherein:
the storage compartment further comprises a biological safety compartment suitable for the storing and containment of biological material in an aseptic manner;
the automated transport unit further comprising a material transfer device configured to extract material from the fluid storage vessel and/or add material to the fluid storage vessel, the material transfer device being arranged to maintain the sterility of the fluid storage vessel;
the automated transport unit further comprising a sterilizing device configured to sterilize a connection port of the fluid storage vessel prior to extracting material from the fluid storage vessel and/or adding material to the fluid storage vessel; and
the automated transport unit further comprising a treatment apparatus configured to perform a treatment on material obtained from the fluid storage vessel and/or to be delivered to the fluid storage vessel.

20. A system comprising:
a fluid storage vessel; and
an automated transport unit, comprising:
a drive mechanism for moving the automated transport unit;
a control system for controlling operation of the automated transport unit;
a power supply for powering the automated transport unit; and
a storage compartment configured to hold a material obtained from the fluid storage vessel and/or to be delivered to the fluid storage vessel;
wherein:
the storage compartment further comprises a biological safety compartment suitable for the storing and containment of biological material in an aseptic manner;
the automated transport unit further comprising a material transfer device configured to extract material from the fluid storage vessel and/or add material to the fluid storage vessel, the material transfer device being arranged to maintain the sterility of the fluid storage vessel;
the automated transport unit further comprising a sterilising device configured to sterilize a connection port of the fluid storage vessel prior to extracting material from the fluid storage vessel and/or adding material to the fluid storage vessel; and
the storage compartment further comprises a temperature controlled area configured to store material during transit.

21. A system comprising:
a fluid storage vessel; and
an automated transport unit, comprising:
a drive mechanism for moving the automated transport unit;
a control system for controlling operation of the automated transport unit;
a power supply for powering the automated transport unit; and
a storage compartment configured to hold a material obtained from the fluid storage vessel and/or to be delivered to the fluid storage vessel;
wherein:
the storage compartment further comprises a biological safety compartment suitable for the storing and containment of biological material in an aseptic manner;
the automated transport unit further comprising a material transfer device configured to extract material from the fluid storage vessel and/or add material to the fluid storage vessel, the material transfer device being arranged to maintain the sterility of the fluid storage vessel;
the automated transport unit further comprising a sterilising device configured to sterilize a connection port of the fluid storage vessel prior to extracting material from the fluid storage vessel and/or adding material to the fluid storage vessel; and the automated transport unit further comprising an analyzing device for analyzing material obtained from the fluid storage vessel.

22. A system comprising:
a fluid storage vessel; and
an automated transport unit, comprising:
a drive mechanism for moving the automated transport unit;
a control system for controlling operation of the automated transport unit;
a power supply for powering the automated transport unit; and
a storage compartment configured to hold a material obtained from the fluid storage vessel and/or to be delivered to the fluid storage vessel;
wherein:
the storage compartment further comprises a biological safety compartment suitable for the storing and containment of biological material in an aseptic manner;

the automated transport unit further comprising a material transfer device configured to extract material from the fluid storage vessel and/or add material to the fluid storage vessel, the material transfer device being arranged to maintain the sterility of the fluid storage vessel;

the automated transport unit further comprising a sterilising device configured to sterilize a connection port of the fluid storage vessel prior to extracting material from the fluid storage vessel and/or adding material to the fluid storage vessel; and the automated transport unit further comprising a treatment apparatus configured to perform a treatment on material obtained from the fluid storage vessel and/or to be delivered to the fluid storage vessel.

* * * * *